(12) United States Patent
Robertson

(10) Patent No.: US 11,517,232 B1
(45) Date of Patent: Dec. 6, 2022

(54) SYSTEMS AND METHODS FOR MOBILE SAMPLE COLLECTION

(71) Applicant: Labrador Diagnostics LLC, Wilmington, DE (US)

(72) Inventor: Channing Robertson, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 490 days.

(21) Appl. No.: 14/936,599

(22) Filed: Nov. 9, 2015

Related U.S. Application Data

(60) Provisional application No. 62/077,023, filed on Nov. 7, 2014.

(51) Int. Cl.
| | |
|---|---|
| *B64C 39/02* | (2006.01) |
| *A61B 5/15* | (2006.01) |
| *G05D 1/00* | (2006.01) |
| *G08G 5/04* | (2006.01) |

(52) U.S. Cl.
CPC .. *A61B 5/150748* (2013.01); *A61B 5/150847* (2013.01); *B64C 39/024* (2013.01); *G05D 1/00* (2013.01); *G08G 5/04* (2013.01); *B64C 2201/128* (2013.01); *B64C 2201/141* (2013.01)

(58) Field of Classification Search
CPC ........ A61B 5/150748; A61B 5/150847; B64C 39/024; G05D 1/00; G08G 5/04

USPC .......................................................... 600/573
See application file for complete search history.

(56) References Cited

U.S. PATENT DOCUMENTS

| | | | | |
|---|---|---|---|---|
| 5,035,865 | A * | 7/1991 | Inaba ................... | A61M 1/0245 422/112 |
| 5,580,789 | A * | 12/1996 | Mancilla ............. | C08B 37/0075 436/18 |
| 9,262,929 | B1 * | 2/2016 | Roy ..................... | G08G 5/0034 |
| 2010/0094166 | A1 * | 4/2010 | Kraemer ............ | A61B 10/0266 600/565 |
| 2010/0285490 | A1 * | 11/2010 | Dees ................ | G01N 33/54373 435/7.1 |
| 2014/0316243 | A1 * | 10/2014 | Niedermeyer ....... | G06Q 10/083 600/407 |
| 2015/0123462 | A1 * | 5/2015 | Kamradt ............... | B64C 39/024 307/9.1 |
| 2016/0018224 | A1 * | 1/2016 | Isler ..................... | G01C 21/005 701/25 |
| 2019/0023392 | A1 * | 1/2019 | Micros ................ | B64C 39/028 |

OTHER PUBLICATIONS

Meadow et al., "Humans Differ in their Personal Microbial Cloud," Sep. 22, 2015, Peerj.*
Ackerman, "Watch This Massive Drone Launch and Recover Another Drone in Flight," Nov. 4, 2015, IEEE Spectrum.*

\* cited by examiner

*Primary Examiner* — Daniel L Cerioni

(57) ABSTRACT

Systems and methods are provided for sample collection from one or more subjects using mobile sample collection devices.

15 Claims, 4 Drawing Sheets

SYSTEMS AND METHODS FOR MOBILE SAMPLE COLLECTION

CROSS-REFERENCE TO RELATED APPLICATION

This application claims priority to U.S. Provisional Application Ser. No. 62/077,023, entitled "Systems and Methods for Mobile Sample Collection" and hereby fully incorporated herein by reference for all purposes.

BACKGROUND

Laboratory testing of blood samples is traditionally based on having a subject or subjects travel to a facility such as a doctor's office or clinical laboratory where the blood sample is collected.

This process of traditional sample collection based on collections at medical facilities creates a legacy system burdened by various limitations that can make the process unnecessarily slow, inconvenient for subjects, and a deterrent to patient laboratory testing compliance.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2014-2015 Theranos, Inc.

DESCRIPTION OF THE SPECIFIC EMBODIMENTS

Figure 1:
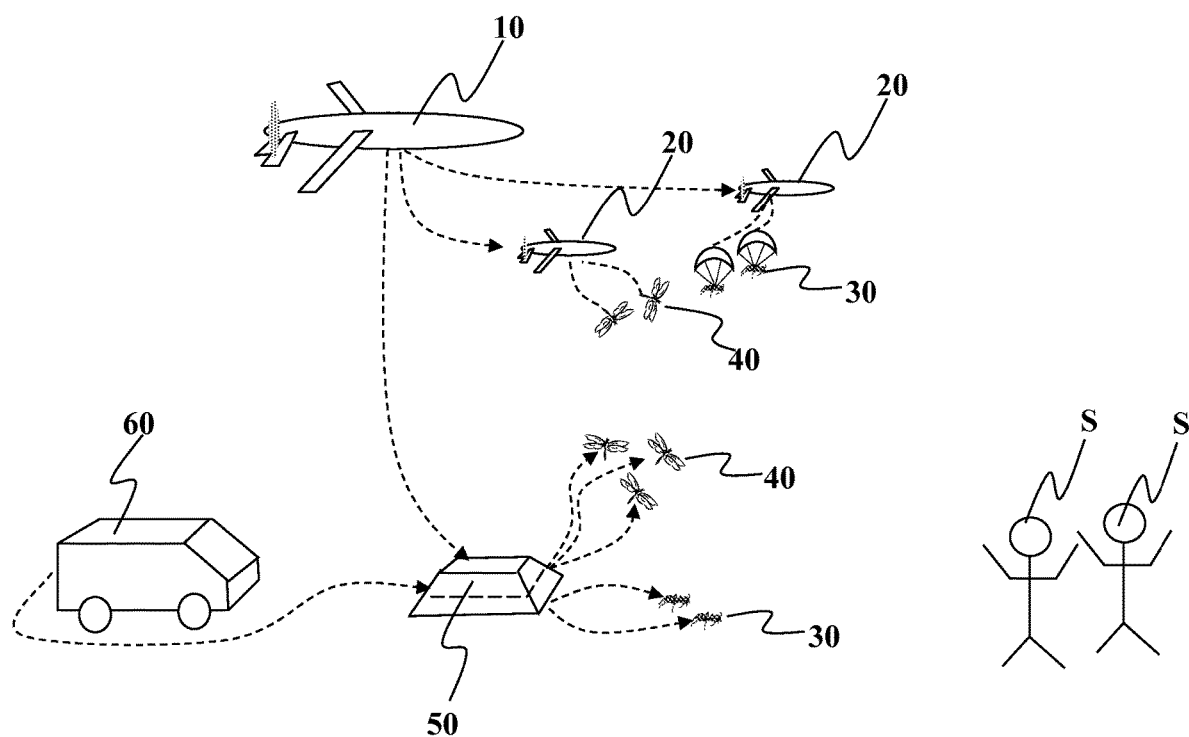
FIG. 1 shows an embodiment of a system as described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by the values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "sampling location" may include without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

The disadvantages associated with the prior art are overcome by at least some embodiments of systems and methods provided herein.

In one embodiment as described herein, one non-limiting example of the system inverts the model of bringing subjects to the location, but instead, the system is designed to bring the sampling location to the subjects. This may be by way of a transport such as but not limited to a blood mobile, autonomous vehicle, or the like. For example, the transport which can move material from one location to another location may be a vehicle, such as a bicycle, car, van, or truck; or a mechanism or vehicle configured to carry a material from one location to another location autonomously (e.g., a conveyor belt, a pneumatic-tube transport system, a driverless vehicle, pilotless aircraft, or other automatic or autonomous transport system). Optionally, the vehicle may use a "nested" system wherein a first transport conveys a plurality of secondary smaller transports to a first location, whereupon the secondary transports are launched to collect samples from subjects. Optionally, some embodiments may have the secondary transports launch tertiary devices for sample collection. This aspect of bringing the sample collection closer to the subject(s) allows for benefits in the sample acquisition part of the system.

In another non-limiting example, embodiments herein may provide sampling techniques for sample collection devices based at least in part on bio-mimicry. This sampling technique may or may not be tied to autonomous devices which travel to sample subjects wherein sampling locations are essentially mobile and movable to the subjects' location. Optionally, these bio-mimicry based techniques may be implemented on devices to be operated by a technician or they may be designed for use on devices that are autonomous. One non-limiting example may use the sampling technique to painlessly extract 5 to 40 microliters of sample from a subject. One non-limiting example may use the sampling technique to painlessly extract 5 to 50 microliters of sample from a subject. One non-limiting example may use the sampling technique to painlessly extract 5 to 60 microliters of sample from a subject. One non-limiting example may use the sampling technique to painlessly extract 1 to 100 microliters of sample from a subject. One non-limiting example may use the sampling technique to painlessly extract 1 to 200 microliters of sample from a subject. One non-limiting example may use the sampling technique to painlessly extract 1 to 300 microliters of sample from a subject. While on the autonomous device, the extracted sample may be mixed with one or more preparatory agents such as but not limited to anticoagulant(s), diluents, or other additives. Optionally, the term painlessly in any of the foregoing examples may be instead replaced with the term undetectably. Optionally, the term painlessly in any of the foregoing examples may be instead replaced with the term unobtrusively. Optionally, the term painlessly in any of the foregoing examples may be instead replaced with the term rapidly.

By way of non-limiting example, a "drone" as used herein may be a mechanical device, electromechanical device, other self-propelled device, or a robotic device that can use one or more modes of transportation such as but not limited to flying, swimming, rolling, crawling, wheeling, and/or other movement mode to travel to a subject. A drone in any of the foregoing descriptions may be configured to be fully autonomous, substantially autonomous operated with limited user oversight, partially remote controlled by a user, or fully remote controlled by a user. Optionally, some embodiments may use a semi-autonomous vehicle that may, in one non-limiting example, be piloted remotely by a human or other controller, but may also have other functions that are autonomous. Optionally, some embodiments may use one or more autonomous vehicles traveling set paths and/or performing certain pre-programmed actions, without adapting to the environment for those pre-programmed actions. Optionally, some embodiments may use autonomous vehicles that can respond to their environment and adapt (avoid obstacles, for instance). In addition to transport capabilities, a drone may also have at least one other capability such as but not limited to video surveillance capability, audio surveillance capability, sample collection, tissue penetration, and/or other capabilities currently known or may be developed.

Optionally, some may test for a simple and/or rapid test initially; if a positive signal is detected, then the system may send more drones or send more sophisticated drones to the subject. Some embodiments may send one or more drones with additional sampling capability or additional sample processing capability. Some embodiments may send a heavy lift drone that can be used to deliver therapeutics and/or return larger samples for processing. Some embodiments may send a longer range drone that can be used to deliver therapeutics and/or return larger samples for processing. Some may send a base station or other forward operating device to or near the location of the first drone to sample the area around that site.

Optionally, the size and weight of the drone may be such that they are less noticeable to the subject. This drives to a certain length scale, possibly smaller than a mosquito. Some embodiments may make autonomous device of a certain length scale with certain attributes such as but not limited to communications (global positioning system [GPS], ability to talk to one another, talk to a base station, guidance, autopilot, etc. . . . ). By way of non-limiting example, one configuration may be one where i) each small flying drone ("gnat") takes the same type of sample→small units each collects a small sample but when combined, they total a large(r) total volume. Optionally, one configuration may be one where ii) each "gnat" takes a different type of sample (blood, sweat, tears, or other bodily fluid)→resulting in greater diversity of sampling. Optionally, one configuration may be one where iii) multiple "gnats" take different types of sample→resulting in greater diversity of sampling and large(r) total volume. In these single subject multiple sampling device configurations, the autonomous sampling devices may communicate with each other, particularly when targeting a common subject. Optionally, some embodiments may have each autonomous sampling devices or subsets of autonomous sampling devices moving to find the target and once the target is found by at least one of the autonomous sampling devices, the others can be informed of the location and then arrive at a later point in time at the desired target.

Sampling Paradigm: Bringing the "Sampling Location" to the Subject

In one non-limiting example as described herein, a system is provided to bring the sampling device to the subject, as opposed to the subject going to "the place" where the sampling devices are located. A sampling technique implemented by a mobile system that brings sampling to the target provides certain advantages such as but not limited to convenience for the subject, increased compliance, and/or improved information gathering for medical records or monitoring. In one embodiment, the system may use sampling devices such as but not limited to autonomous sampling devices that are a) autonomous for the sample collection and/or b) autonomous for transport to the location of the subject(s).

In one embodiment, a drone may be used as the autonomous sampling device that can bring the sample collection process to the location of the subject. By way of non-limiting example, a "drone" as used herein may be a mechanical device, electromechanical device, other self-propelled device, or a robotic device that can use one or more modes of transportation such as but not limited to flying, swimming, rolling, crawling, wheeling, and/or other movement mode to travel to a subject. A drone in any of the foregoing descriptions may be configured to be fully autonomous, substantially autonomous operated with limited user oversight, partially remote controlled by a user, or fully remote controlled by a user. Optionally, some embodiments may use a semi-autonomous vehicle that may, in one non-limiting example, be piloted remotely by a human or other controller, but may also have other functions that are autonomous. Optionally, some embodiments may use one or more autonomous vehicles traveling set paths and/or performing certain pre-programmed actions, without adapting to the environment for those pre-programmed actions. Optionally, some embodiments may use autonomous vehicles that can respond to their environment and adapt (avoid obstacles, for instance). In addition to transport capabilities, a drone may also have at least one other capability such as but not limited to video surveillance capability, audio surveillance capability, sample collection, tissue penetration, and/or other capabilities currently known or may be developed.

In one non-limiting example, the mobile sample collection process herein may include traveling to the general vicinity of subjects, finding the subjects, accessing them, obtaining at least one sample, and/or retrieving the sample, etc. . . . .

Although some embodiments may implement the process using a single drone or even multiple drones, some embodiments may optionally use nested drones or nested vehicles concept wherein the drone(s) or vessel(s) are combined in one or more configurations wherein the combined entity provides capabilities that may be greater than the capabilities of any one of the drone(s) or vessel(s) used individually. In one non-limiting example, the nested drones or nested vehicles may be in the form of sisterships, motherships, daughterships, or any single or multiple combination of the foregoing. Various single or multiple combinations of sisterships, motherships, daughterships, or the like can result in greater area of coverage, enhanced "on-station" or "on-duty" time, enhanced range, or other operational capability as compared to the abilities of any such device or vehicle on an individual basis. Optionally, in some embodiments, the mothership can be: autonomous, semi-autonomous, or remote controlled. Optionally, in some embodiments, the mothership can: transport vehicle (carries multiple drones to dispersion site, collects them after use); provide energy (recharging drones); perform sample collection from returning drones; or re-fit drones with equipment for further deployment. Optionally, in some embodiments, the collection site may be for combining samples from multiple drones, or segregating drones by location, sample type, or other criterion. Optionally, for quality control, inspecting drones/samples for selection or quality or volume or any initial criteria. Optionally, at least one embodiment may provide a preparatory lab—pre-processing samples (filtering, centrifuging, coagulating, heparinizing, etc.) on the drone, mothership, or base station. Optionally, at least one embodiment may provide an analytical lab (performing one or more analytical steps).

Optionally, when using multiple autonomous devices, swarm technology can be used to coordinate activity between the multiple devices and/or vehicles to provide greater survivability, reduced energy consumption based on coordinated activity (drafting, some may fly in formation for the drag reduction, coordinated motion for general benefit, etc. . . . ), increased area coverage based on coordinated activity, other operational benefit based on coordinated activity, etc. . . . . It should also be understood that these devices and/or vehicles can communicate directly with one another, or indirectly such as but not limited to a communicating with a central hub, communicating with a relay station, communicating through dead-drop location(s), or other indirect communicating techniques. Optionally, some embodiments may use the concept of swarm technology to help the autonomous device(s) and/or vehicle(s) aggregate and/or congeal to act as a single unit or organism. For at least one embodiment herein, the swarm of drones may be one wherein the number to be deployed are calculated based on a predicted "loss" factor and the number of drones desired to cover a certain geographic area (such as drones per square mile) or the number of potential target subjects (such as subjects per square mile).

In some instances, the units can communicate with one another if need be or if one fails to receive its instructions from a central command. Some embodiments may be configured to be designed with a certain quantity of autonomous devices that are understood to not return. In one non-limiting example, this can be a statistically deployed concept wherein based on a plurality of factors such as but not limited to weather condition, time of year, geography, urban vs rural environment, animal activity, human activity, government related factors, type of mission, desired area of coverage, and/or other factors, the number and/or types of autonomous device to be used can be predetermined.

In one embodiment, the mobile sampling system may combine autonomous technology with one or more swarm technologies, one or more motive/movement technologies, and/or one or more sample acquisition technologies.

Referring now to FIG. 1, at least one embodiment of a mobile sampling system will now be described to deploy sampling device(s) to at least one location where subject(s) are located. In this non-limiting example, an airborne transport vehicle 10, which may or may not be autonomous, is used to transport at least one of several devices to locations near subjects S. Although only one airborne transport vehicle 10 is shown, it should be understood that some embodiments may use a plurality of airborne transport vehicles 10 to increase the number of devices being deployed. Some embodiments may use a pilot-less airborne transport vehicle that is remotely operated by one or more human operators. Optionally, some embodiments may use a pilot-less airborne transport vehicle that is autonomous without human interaction. Optionally, some embodiments may use a pilot-less airborne transport vehicle that is a combination of being substantially autonomous that incorporates remote operation by one or more human operators for certain task(s).

As seen in FIG. 1, one embodiment may optionally use the airborne transport vehicle 10 to deploy one or more additional airborne vehicles 20. In some embodiments, these additional airborne vehicles 20 can perform the sampling on the subject S. Optionally, some embodiments may have the additional airborne vehicles 20 deploy still further devices 30 and 40. In one embodiment, the devices 30 are ground-based sampling device that may have parachute or other soft-landing feature to allow for airborne delivery of these ground-based devices. The ground based devices 30 can then crawl, roll, or otherwise move on the ground to reach a desired target area near the subject S. Optionally, some may reach a target site on the subject S using crawling, rolling, wheeling, climbing, or other movement technique. As seen in FIG. 1, some embodiments may deploy multiple devices 30 to cover a target area.

Optionally, the device 40 may be yet another airborne device that can fly to reach a desired target area near the subject S. Optionally, some may reach a target site on the subject S. As seen in FIG. 1, multiple airborne devices 40 may be deployed. As seen in FIG. 1, the device 40 may be a flying device that uses a flapping-wing type motion to allow for flight of the device. Optionally, other embodiments of flying device 40 may use other types of motive force such as but not limited to jet, propeller, rocket, scram, and/or other propulsion techniques, alone or in single or multiple combination to provide flight capabilities to the device 40.

FIG. 1 shows a still further embodiment wherein the airborne transport vehicle 10 deploys at least one base station 50 to a location where the base station 50 can deploy ground-based devices 30 and/or flying devices 40. As seen in FIG. 1, some embodiments may use at least one ground transport vehicle 60 to deploy one or more of the base stations 50. This use of at least one base station 50 may be one that operates on its own or in combination with other base stations 50. It should also be understood that some embodiments may use the base station 50 as the sampling device return and/or deployment locations. Optionally, some embodiments may include sample processing and/or sample analysis capabilities on the base station 50. In one non-limiting example, the base station 50 may include at least one sample processing unit as described in U.S. patent application Ser. No. 13/769,820 filed Feb. 18, 2013 entitled Systems and Methods for Multi-Analysis, which is hereby fully incorporated herein by reference for all purposes. Optionally, the base station 50 may include at least one sample inspection unit as described in U.S. Patent Application Ser. No. 61/944,557 filed Feb. 25, 2014 entitled Systems, Devices, and Methods for Sample Integrity Verification, which is fully hereby incorporated herein by reference for all purposes. In one non-limiting example, a base station 50 can be configured to perform a more involved sample processing and/or provide a sample integrity verification function. Optionally, some embodiments may have a base station 50 configured with at least one sample separation device, such as but not limited to a centrifuge, a magnetic separation device, or other formed component separation device known or may be developed in the future.

By way of non-limiting example, one may deploy ground-based device(s) 30 and/or flying device(s) 40 from at least one airborne transport vehicle 10, collect sample from a subject S, and then return to at least one base station 50. Optionally, some embodiments may operate where ground-based devices 30 and/or flying devices 40 are deployed by the base station 50 and return to the same or different base station 50. Optionally, some embodiments may operate where ground-based devices 30 and/or flying devices 40 are deployed by the base station 50 and are collected by the airborne transport vehicle 10 and/or the ground-based transport vehicle 60. Optionally, some embodiments may use a still additional vehicle (not shown) for retrieving one or more of the devices 30 or 40 after they have obtained their samples. Optionally, some embodiments may use satellite control, high altitude floating or flying craft control, or other non-ground based techniques for control and/or deployment.

Referring now to FIG. 2, a still further embodiment will now be described regarding the deployment of sampling device(s) to at least one location where subject(s) are located. FIG. 2 shows an airborne transport vehicle 100 which has a vertical hovering capability. As seen in FIG. 2, the airborne transport vehicle 100 can transition from level flight to a more vertical orientation as indicated by arrow 102 to facilitate delivery of its payload to a desired location. FIG. 2 shows that the payload, which in this non-limiting example is a base station 50, can be lowered by rope, dropped, parachuted, or otherwise delivered as indicated by arrow 104. Optionally, in embodiments, the base station 50 may have its own propulsion system to enable movement such as but not limited to ground transportation, flight, or other transport technique. Optionally, in embodiments, the base station 50 may discard certain portions of the base station 50 such as but not limited to used containers, used fuel containers, used batteries, used landing gear, or other portion(s) that may be discarded to reduce weight for any further propulsion by or transport of the base station 50.

Although not limited to the embodiment shown in FIG. 2, the airborne transport vehicle 100 may have a quad-fin with a single, dual, tri, or quad propeller or duct fan design that can provide sufficient thrust and control capabilities to transition from level flight to a vertical hover. When in a vertical hover, the airborne transport vehicle 100 can directly deploy ground-based devices 30 and/or flying devices 40. Optionally, the airborne transport vehicle 100 can deploy at least one base station 50 which can then deploy ground-based devices 30 and/or flying devices 40 from the base station 50. Optionally, some embodiments may use other airborne transport vehicles such as but not limited to gyrocopters, gyroplanes, autogyros, helicopters, quadcopters, tiltrotor aircrafts, tiltwing aircrafts, balloons, lighter-than-air crafts, airship, dirigible, VTOL aircraft, or other vertical hover capable devices in place or along with the vehicle design shown in FIG. 2.

In terms of implementation of one or more of the embodiments herein, one aspect is finding the target such as but not limited to locating a person, a target site on the subject S, and/or a general area where subjects S may be located for retrieving the sample using the sampling device. Another aspect is acquiring the sample into the device (getting the sample from the subject into the fluid compartment on or associated with the sampling device). Once a sample has been acquired, retrieval of the sample is a still further aspect.

In one non-limiting example, location acquisition (for targeting or retrieval) may be by one or more of the following: vision, magnetically, prior GPS coordinates, chemically, electrically, radar, sonar, GIS systems, mapping, and/or other targeting system. Some may use targeting based on features such as but not limited to gas output, thermal signature, $CO_2$ output, scent based characteristics, chemical, UV, anything in the EM spectrum, or other signature characteristic of the target. In some embodiments, acquisition may involve waiting at opportunistic locations for subjects to walk by or be positioned for sampling. By way of non-limiting example, some may involve being positioned on a tree branch, perch, overhang, or other location above the subject S. In some embodiments, tentacles, webs, strings, or attachments lines may be deployed in a hanging manner to assist in getting the sampling device to the subject S. In one embodiment, the device may acquire sample from a subject's finger or hand. In one embodiment, the device may acquire sample from a subject's forearm. In one embodiment, the device may acquire sample from a subject's ear lobe. In one embodiment, the device may acquire sample from a subject's ear cheek. In one embodiment, the device may acquire sample from a subject's buttock.

In one embodiment, offloading the sample from the autonomous collection device comprises at least one step of taking a container from the device and transferring to a sample processor. Optionally, the autonomous collection device comprises at least a tank/bladder, wherein extraction may be by way of removing the entire tank/bladder or by removing the contents therein by squeezing the tank or bladder, by suction, by siphon, or by other known technique or technique to be developed in the future. Optionally, the autonomous collection device comprises at least a spout, a portal, a pierce-able rubber stopper, a pierce-able septum, a self-healing septum, a drain, a valve, or other access area for sample collection.

In another non-limiting example, one aspect may be getting the sample physically back to a desired location, retrieval site, base station, and/or a mothership. Optionally, some embodiments may, instead of returning with the physical sample, may provide electronic or other non-tangible information regarding the sample. In one non-limiting example, the device may collect sample and then either stay or move to a location where it can fully or partially process the sample and then transmit the sample data wirelessly, by other non-wired technique, or use other information transmission technique that may be developed in the future, to send data to an external device that collects such information.

Optionally, a mothership may deploy a base station or similar processing station from which the sample units return to process a sample from which electronic data is transmitted. In one embodiment, the mothership may deploy a base station and then move on to deploy one or more other base stations. In one non-limiting example, the base station is disposable and will not be retrieved by the mothership. In one non-limiting example, such a base station will serve to send the data back from any returning collection drone(s).

One aspect is to decouple collection and processing of sample(s) in terms of space and time. Thus, these may be to use one type of device to collect the sample and then use a different type of device to perform processing of the sample. Optionally, these pieces can be combined together for a device that collects the sample and also does processing the sample.

In another embodiment, reduced sample volumes is a still further aspect that can enable the use of small drones for sample collection, because at least in part, the payload for such a sample is reduced to a smaller volume that is more transportable relative to conventional analyzers which would require a larger sample and thus a larger drone to acquire and transport such larger sample. In one embodiment, the sample collection is for a sample volume of 500 uL or less. Optionally, the sample collection is for a sample volume of 400 uL or less. Optionally, the sample collection is for a sample volume of 300 uL or less. Optionally, the sample collection is for a sample volume of 200 uL or less. Optionally, the sample collection is for a sample volume of 100 uL or less. Optionally, the sample collection is for a sample volume of 80 uL or less. This reduced volume more enables the embodiments here to use tick or mosquito type sample acquisition techniques because the desired sample size is so small.

Figure 2:
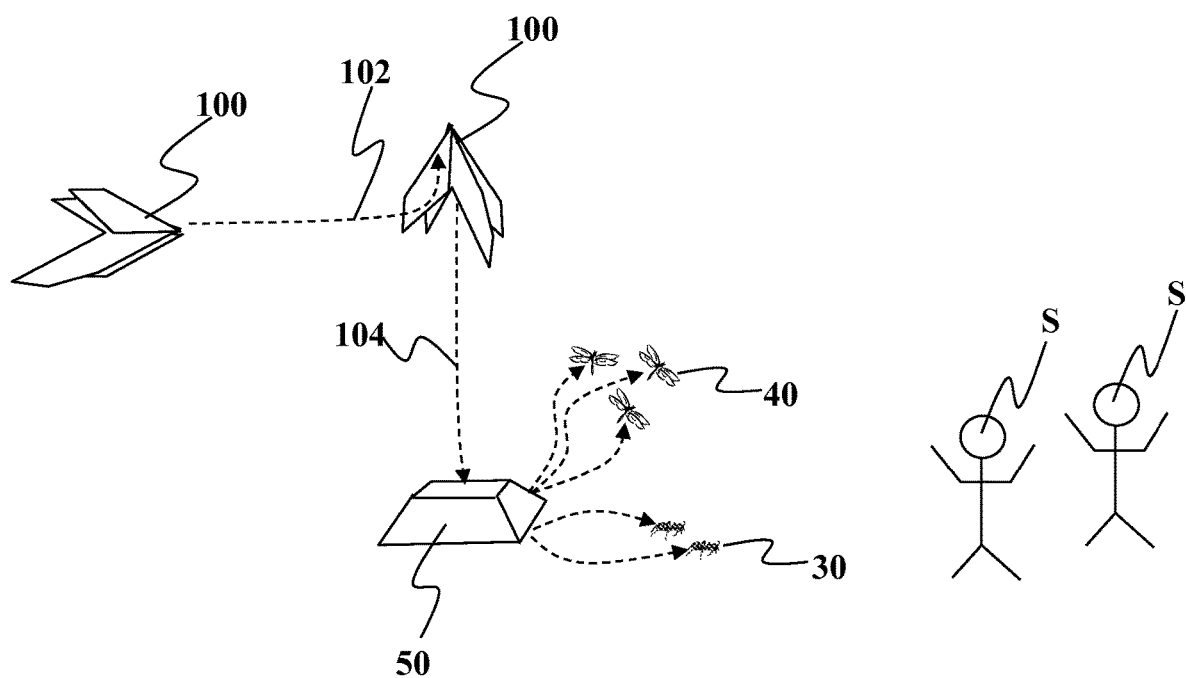
FIG. 2 shows an embodiment of a system as described herein.
Figure 3:
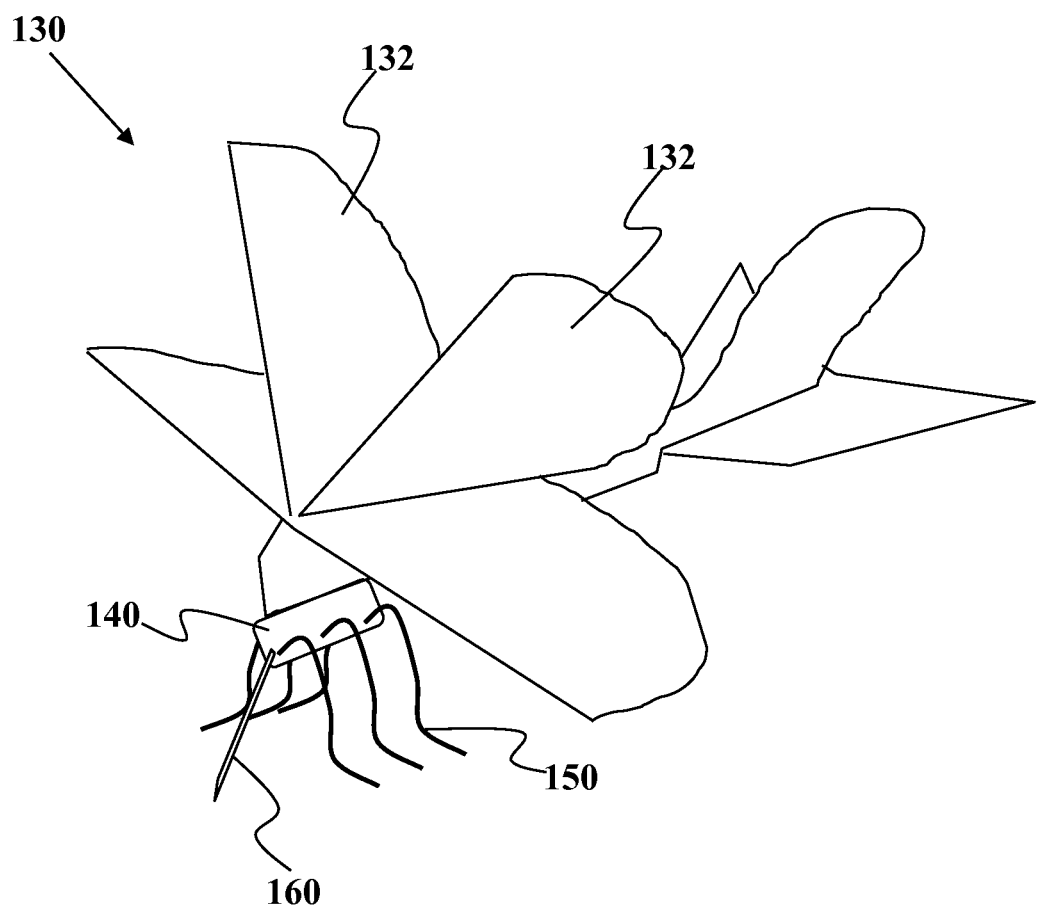
FIG. 3 shows an embodiment of a device as described herein.

Referring now to FIG. 3, one embodiment of an autonomous sampling device will now be described. By way of non-limiting example, the embodiment shown in FIG. 3 may be used as one of the flying sampling devices 40 shown in FIGS. 1 and 2. In one non-limiting example, the flying sampling device 130 may be an autonomous device that is a winged flight device using flapping motion of wings 132 to generate motive force. This non-limiting example of autonomous sampling device 130 includes a sampling capsule 140 that may be used to retain any captured sample. By way of non-limiting example, the sampling capsule 140 may have a chamber at sub-atmospheric pressure that can be used to draw sample into the chamber of the capsule 140. Optionally, other embodiments may use a vacuum pump, syringe, or other type of device to provide force to direct sample into the sampling capsule 140. Optionally, the autonomous sampling device 130 may also include ground transport motive devices 150 such as but not limited to wheels, tracks, legs, or other apparatus for providing ground or surface based movement.

In this non-limiting example of FIG. 3, at least one tissue penetrating member 160 may be mounted on the autonomous sampling device 130. In one embodiment, the tissue penetrating member may have a needle-type design that can be used to direct sample into the sampling capsule 140. Optionally, some embodiments may use one or more penetrating members such as but not limited to micro needles to create an access route on the subject from which another instrument such as but not limited to a capillary tube, vacuum tube, or other sample collect instrument can collect the sample using the access route or sample pooled or formed at the access route site. The sampling capsule 140 may include one or more preparatory materials such as but not limited to anticoagulant(s), diluent(s), or other additive(s). Some embodiments may include such materials in the lumen or channel walls of the tissue penetrating member 160. Optionally, in embodiments, there may be connections to a reservoir for one or more preparatory materials or for other materials.

In some embodiments, after collection of sample into the sampling capsule 140, certain parts of the autonomous device 130 may be discarded to reduce the weight of the return vehicle. Some may discard the tissue penetrating device 160 and/or the ground-based transport mechanism 150. Optionally, some may discard the flight portion of the autonomous device 130 and only return the capsule 140 with ground based transport mechanism 150. In some embodiments, a separate return vehicle may arrive by surface or air to retrieve the sample capsule 140.

Figure 4:
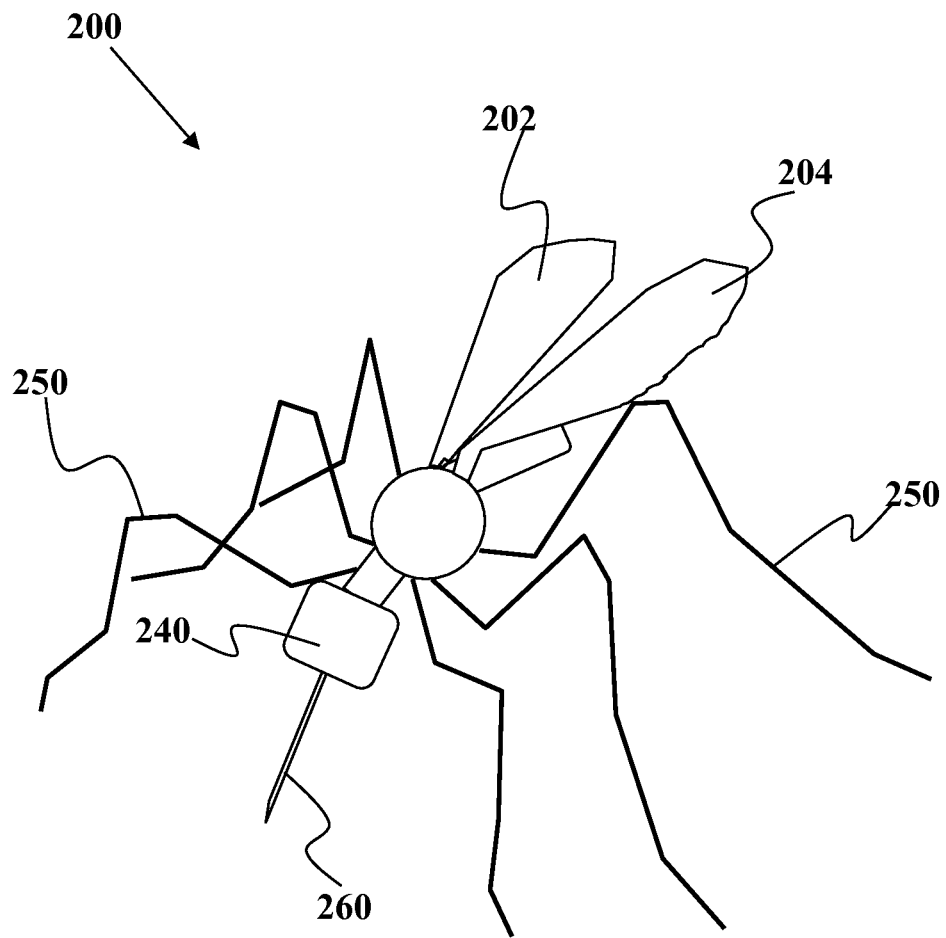
FIG. 4 shows an embodiment of a device as described herein.

Referring now to FIG. 4, a still further embodiment of an autonomous sample collection device 200 will now be described. Again, this embodiment of FIG. 4 may also be used as one of the flying sampling devices 40 shown in FIGS. 1 and 2. FIG. 4 shows an autonomous sample collection device 200 that uses flapping wings 202 and 204 to provide flight to the device. Optionally, other embodiments may include additional flapping or fixed wings (not shown for ease of illustration) in addition to the flapping wings 202 and 204. Some embodiments may use propeller, duct fan, jet, or other forms for propulsion in place of or in addition to the flapping wings 202 and 204.

As seen in FIG. 4, the autonomous sample collection device 200 may have a directable sample capsule 240 with at least one steerable portion coupled to a tissue penetrating member 260. In one embodiment, the tissue penetrating member may have a needle-type design that can be used to direct sample into the sampling capsule 240. Optionally, some embodiments may use one or more penetrating members such as but not limited to micro needles to create an access route on the subject from which another instrument such as but not limited to a capillary tube, vacuum tube, or other sample collect instrument can collect the sample formed at the access route entry site. In some embodiments, after collection of sample into the sampling capsule 240, certain parts of the autonomous device 200 may be discarded to reduce the weight of the return vehicle. Some may discard the tissue penetrating device 260 and/or the ground-based transport mechanism 250. Optionally, some may discard the flight portion of the autonomous device 200 and only return the capsule 240 with ground based transport mechanism 250. In some embodiments, a separate return vehicle may arrive by surface or air to retrieve the sample capsule 240.

One embodiment may configure the drone to certain length/weight scales for mobility for sample collection and/or drug delivery. For example, some may only use drones of 10 mm or less. Optionally, some may use drones that are only 5 mg or less. Some embodiments may be aggregated (like a fireworks shell) that scatter when activated. Optionally, different drones have different tasks that can self-assemble into a larger operating organism.

In one embodiment, a single device may also retrieve 10 or more samples if each of the samples is small. In one embodiment, a single device may also retrieve 5 or more samples. Optionally, the single device may retrieve at least two samples, each sample from the same or different subject. Optionally, some devices may retrieve different types of samples from the subject. Optionally, some embodiments may extract the same or different types of sample from at least two different target sites on the subject. In terms of identification, some embodiments may identify a generic target (any human, any animal, any moving object) or a specific target (facial recognition; iris scan; biometrics; chemicals; chemical signature, DNA). Optionally some embodiments may perform target identification after the sample has been acquired. Various techniques may be used for target classification and where appropriate for target uniqueness.

Optionally, some embodiments may detect a target based on at least a microbial signature associated with a target, such as may be found in microbial cloud(s) generated by or associated with the target. Dispersal of microbes between humans and the built environment can occur through direct contact with surfaces or through airborne release; the latter mechanism remains poorly understood. Humans emit upwards of $10^6$ biological particles per hour and have long been known to transmit pathogens to other individuals and to indoor surfaces. Humans can emit a detectible microbial cloud into surrounding indoor air, wherein such clouds may be sufficiently differentiated to allow the identification of individual occupants. Optionally, some settled particles surrounding a target may also leave detectable identifiable characteristics. Most occupants could be clearly detected by their airborne bacterial emissions, as well as their contribution to settled particles, within 1.5-4 h. Bacterial clouds from the occupants were statistically distinct, allowing the identification of some individual occupants. It should be understood that an occupied space is microbially distinct from an unoccupied one, and that individuals release their own personalized microbial cloud.

In one embodiment, at least one of the autonomous device collect microbial cloud information to determine if the subject is the desired target. In one embodiment, there is an initial set-up phase wherein subjects in the program will provide a microbial cloud sample to "register" that subject in the system. Optionally, other characteristics of the subject such as but no limited to height, weight, sex, profile, thermal image, picture, or the like may also be associated with the microbial cloud sample to more confidently confirm a target.

Sample Processing

In one embodiment, the analysis may be only a partial processing, partial analysis, and/or only preliminary, threshold work in terms of what can be done on the base station.

After initial base station analysis, only some portion of the processed samples are then further transmitted or transported for analysis at a further processing station. Some may acquire information about a subset of analytes that correlate or relate to those other analytes of interest. Based on initial screening, it can be determined what percentage requires further sampling. Optionally, some embodiment may only do the initial sampling and not do any further processing if the initial sampling does not indicate a further requirement for additional sample processing.

Optionally, sampling theory and statistics is used as part of one implementation in terms of disease or other outbreak detection. In one embodiment, sampling theory and statistics can be used to determine where to further sample based on a first round of sampling or prior to the start of sampling. Sampling theory and statistics can also be used to adjust sampling strategy based on real-time information sent back about partial analysis, on board analysis, and/or remote analysis. Optionally, this analysis piece could take place on a mothership or a base station and data can be streamed to another location to evaluate real-time data received from the field. Optionally, a physical sample could be brought back or telemetry or other data can be sent regarding the sample. Optionally, some embodiments may configure the autonomous sampling devices to collect sample and using a wireless or other communication technique, transfers sample information from the device to another location and the sampling device is not physically retrieved or returned to its launch site or a collection. Some embodiments may use variations of the non-return of sample configuration wherein in a relay manner, some collection devices may collect sample and then transfer data and/or the sample to another device which then continues to process and/or return the sample to launch or collection site.

In one embodiment, the population to be sampled is one that has signed up (physically or electronically) to be sampled. This may occur by opt-in type paradigm. Optionally, some may use an opt-out paradigm. In one embodiment, an example of such a group of subjects may be all patients associated with a particular health insurance company, doctor group, medical group, or other affiliation (health-related or otherwise). Optionally, it can be by some other segmentation. In this manner, the population to be sampleD is not a random one but is one that has given permission for the sampling to occur. This may facilitate the geography of where the subjects are and simplify target acquisition. Optionally, some embodiments may further have subjects wear beacons, identifiers, other devices, other materials, or other items that may be used to help facilitate target acquisition by the sampling device. For example, some may wear Bluetooth standard transmitters, infrared transmitters, or other device now known or to be developed in the future to transmit non-human audible signal to facilitate sample acquisition. Deployment on a military environment may be useful due to greater ease of initial agreement to such a sampling paradigm. Most members of military already have DNA on file so it is easier to track back where sample came from based on DNA in the same. So this can be used with an existing database of individuals already with info on file. Optionally, some may opt in to join this program.

In one non-limiting example, there is an option for sampling weekly, monthly, or other interval. Some may be at no cost. Some embodiments may be configured where the user receives discounts, reduced cost, or free item(s) based on continued participation in the sampling program. In one non-limiting example, such sample collection may be occurring and the subject may not even know it. In one non-limiting example of the paradigm, the collection will happen and the subject will be informed if something important is detected. This may be a way for insurance companies or military to track their population's health. By way of non-limiting example, this may occur on ships, on the battlefield, on a military base, or other facility as desired.

Optionally, the autonomous sample and autonomous transport sampling devices may be used alone or in conjunction with other devices. For example, some embodiments herein may be configured to locate sample collection device(s) as part of objects that a user may touch everyday such as but not limited to handle bars, stair rails, bathroom toilet seat, floor of bathtub or shower, weighing surface of weight scale, steering wheel of a vehicle, seat on a vehicle, sofa, chair, and/or the like. Optionally, one may go for using a sampling device in an object that everyone contacts on a weekly or daily basis. Some embodiments of a sampling device on a device that a user regularly comes into contact such as but not limited to the toilet seat or a weight scale where user steps or sits on the unit may also use weight as one factor to confirm who in the household is on the device and is being sampled.

In one non-limiting example, a subject's bodily fluid is being tested hourly or other frequent interval without the subject's explicit knowledge. In one non-limiting example, a subject's bodily fluid is being tested hourly or other frequent interval at the subject's location and with the subject's explicit knowledge because they have given permission for such testing. This may be to monitor the subject's health. One would look for outliers, look for trend, or other features in the analyte measurements that take the sample out of the background of normal readings, wherein normal may be defined for that particular individual or for a group of subjects having common characteristics (weight, age, sex, etc. . . . ). When appropriate, the system may be configured to notify doctors, insurance companies, or whoever else would benefit from knowing or who are on a pre-determined or real-time determined list of people or entities to contact.

In one non-limiting example, this notification is ideally occurring before the subject is symptomatic such as but not limited to before there is a fever, before there is a headache, before the body is trying to address this issue, etc. . . . . This analyte testing may be for cancer biomarkers, neuro-degenerative disease biomarkers, genetic marker, etc. . . . .

In one aspect, one embodiment of the system is designed to sample, to measure, and to report. In such an embodiment, the system does not provide a diagnosis.

In one non-limiting example, one option is to park vehicles with the sampling technology close to subject location(s). Optionally, one can pre-position vehicles with the sampling technology close to subject location(s). In another embodiment of a blood-test-on-wheels system, an autonomous vehicle may be used to transport a device to the subject and then collect the blood sample.

Optionally, some embodiments may be designed with an on-demand software aspect wherein a user through a mobile application or other software for requesting mobile sample collection on-demand. By way of non-limiting example, the mobile application can also provide subject location information to the mobile sample collection unit. In one embodiment, the mobile device software application can also show to the subject the location of near-by sample collection units.

Optionally, one could also deploy by a courier to bring the sample collection device to the recipient. In one non-limiting example, the courier may deliver a self-collection kit wherein the subject will draw the sample from themselves. Optionally, the system may mail or otherwise deliver the drone the initial leg and then drone travels the other leg or final leg to a target site on the subject.

Sampling Technology Based on Bio-Mimicry

In one non-limiting example, the sample acquisition from a subject may be in a form that is based at least in part on bio-mimicry of tick, leech, mosquito, or other natural blood sampler for sampling purposes.

For example, the sampling device can have at least one tissue penetrating member that moves with an oscillating motion for blood sampling. Some can deliver an anesthetic and/or anti-coagulant. In one embodiment, a sheath can be used to provide strength and/or support over or with the sampling tip. In one non-limiting example, the penetrating head oscillates at frequency such as but not limited to 10 to 30 Hz. The tissue penetrating head saws instead of punctures because a long narrow tube would buckle. Thus, the sampling device may use a non-ballistic penetrating member.

Optionally, some embodiments could be designed to leave something behind such as but not limited to an RFID chip or other tag, wherein the sampling device is not limited to just sampling. Some embodiment of the sampling device can use multiple tubes such as but not limited to one for sampling one for delivery. Not only sampling blood but could be interstitial fluid or tissue sensor.

Once autonomous device is on the subject, it may need to find skin (or optionally, go through clothing, even though this increases the length of the material that the acquisition device would penetrate). Machine learning where the autonomous can recognize certain texture such as but not limited to not drilling on a callus or other characteristics that may be associated with "dry holes" that do not yield sample fluid. Optionally, some embodiments may have the autonomous device travel to a designated location at the target's location, such as a docking area or the like, where the user will then provide a target surface for sampling. By way of non-limiting example, the autonomous device may travel to connect with a seating surface where it is expected that the subject will sit or otherwise come into contact. Optionally, the seating surface may be a toilet seat wherein either a portion of the seat, an underside of the seat, or housing nearby can be the docking location for the autonomous device to arrive. In this manner, the autonomous device does need to further seek the subject once the autonomous device arrives at the desired address/location. Optionally, other surfaces such as arm surfaces, hand surfaces, finger surfaces, pillows, or another direct-body-contact surface(s) that may be found in a home, hospital, school, medical facility, wellness facility, or the like.

In one embodiment, not only does drone get to the target, but then also gets to the sampling site on the target. One further embodiment may use further techniques or refinements to acquire the sample. There may be a grappling or other type movement on the subject to reach a target site. Some may use other types of mobility techniques while on the target. Optionally, some may have the ability to detect if they are on the skin or not (or possibly the desired body part). Once they are at the target site, then can go into the drilling or sampling motion. Some may know when it has intercepted the capillary; some may volume measure of sample (by volume or weight). Some embodiments may use a drilling/dry hole type model where it moves to a next site if unsuccessful at a first site. Optionally, some may fly and land on a surface and then crawl to the subject. Some may land and remain in the shower or bathroom or other desired area to facilitate sample collection. Optionally, some may also be configured to work in an aqueous environment.

Optionally, some portions of an autonomous sampling device are single use. Optionally, some portions of an autonomous sampling device are reusable. Optionally, in device configurations where certain parts are disposable, the sampling device may use the disposable part(s) during the transport and/or sample acquisition phases. Once those phases are completed, the disposable parts are discarded or left behind so that a more lightweight portion is returned to the mothership or base. It should be understood that in some embodiments, the reduced weight is useful to accommodate the increased weight associated with the sample collected from the subject.

In one embodiment discussed herein, a method is provided comprising: providing a plurality of autonomous sampling devices for sample collection, calculating a predetermined quantity of autonomous sampling devices to deploy for sampling based at least on two of the following: size of a geographic area to target, estimated number of subjects in the geographic area, weather conditions in the geographic area, time of year, range of drone devices, or predators in the geographic area. The method includes deploying a sufficient number of the autonomous sampling devices equal or exceeding the predetermined quantity to acquire sample from subjects in the geographic area; and using at least one of the autonomous sampling devices to acquire sample from at least one subject in the geographic area.

Optionally, any of the embodiments herein may further include one or more of the following features. For example, the method may further comprise deploying at least one base station to the geographic area for the autonomous sampling devices to return after sample collection. Optionally, the base station is self-propelled. Optionally, at least a portion of the base station may be discarded to facilitate base station self-propulsion. Optionally, the autonomous sampling devices operate in a swarm. Optionally, the autonomous sampling devices operate in a swarm wherein the autonomous sampling devices communicate with each other regarding at least positioning between devices for crash avoidance. Optionally, at least one of the autonomous sampling devices comprises a ground-based drone. Optionally, at least one of the autonomous sampling devices comprises a flying drone. Optionally, at least some of the autonomous sampling devices detect a subject's microbial cloud. Optionally, a recovery unit can be deployed to recover autonomous sampling devices lost or disabled. Some of the recovery units may use a magnetic technique to locate the devices. Optionally, the method comprises having targets in the geographic area registered in a computer database with location and identifier information. Optionally, at least some of the autonomous sampling devices have a docking location near their target.

In another embodiment discussed herein, a method is comprising: providing a plurality of self-transporting sampling devices for sample collection, monitoring pandemic progress based on data returned from the sampling devices; and based on the monitoring, sending additional sampling devices to another geographic area for monitoring.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that although many embodiments describe sampling from a subject, it should also be understood that sampling could be of the food chain, environmental materials, farms which sample for pests, water samples, other fluid sitting around which may have a contagion, or other similar uses are not excluded. By way of non-limiting example, in at least one embodiment, the linkage is a micro sample that is small enough for the autonomous sampling device to return and is not limited to the type of sample (biological or non-biological) that is being collected.

A still further embodiment may use a plurality of mobile devices to distribute self-testing kits over a geographic area that one desires to monitor. In one non-limiting example, the self-testing kit may include a sampling device and sample container that the subject operates per instructions-for-use included with the self-testing kit. Once a sample is collected, the subject can either mail the sample back (some embodiments may include prepaid return mailers) or some embodiments may have mobile devices come by to pick-up the samples. Optionally, other embodiments may have self-testing kits that include autonomous sampling device(s), wherein a subject's action to open and/or activate the kit, is the subject's acknowledgement to proceed with testing which initiates the autonomous sampling device to perform sample collection. The sample may be returned using one or more of the techniques as described herein.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes:

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for."

What is claimed is:

1. A method comprising:
providing a plurality of autonomous sampling devices for sample collection, wherein each of the autonomous sampling devices includes a sample capsule coupled to a tissue penetrating member;
deploying at least a predetermined number of said autonomous sampling devices to acquire sample from subjects in a geographic area; and
using at least one of said autonomous sampling devices to acquire sample from at least one of said subjects in the geographic area by traveling to and connecting with a seating surface having a docking location for the at least one autonomous sampling device and wherein said at least one of the subjects comes into contact with the seating surface having the docking location.

2. The method of claim 1 further comprising also deploying at least one base station to the geographic area for the autonomous sampling devices to return after sample collection.

3. The method of claim 2 wherein the base station is self-propelled.

4. The method of claim 3 further comprising discarding at least a portion of the base station to facilitate self-propulsion.

5. The method of claim 1 wherein said autonomous sampling devices operate in a swarm.

6. The method of claim 1 wherein said autonomous sampling devices operate in a swarm wherein said autonomous sampling devices communicate with each other regarding at least positioning between devices for crash avoidance.

7. The method of claim 1 wherein at least one of the autonomous sampling devices comprises a ground-based drone.

8. The method of claim 1 wherein at least one of the autonomous sampling devices comprises a flying drone.

9. The method of claim 1 further comprising using a recovery unit deployed to recover autonomous sampling devices lost or disabled.

10. The method of claim 1 further comprising having targets in the geographic area registered in a computer database with location and identifier information.

11. The method of claim 1 wherein at least some of the autonomous sampling devices have a docking location near their target.

12. The method of claim 7 wherein the ground-based drone is deployed to a designated location by a flying transport device.

13. The method of claim 1 wherein the seating surface is part of a toilet seat.

14. The method of claim 1 wherein the sample capsule contains an anticoagulant.

15. The method of claim 1 where the seating surface is at a designated location known to the one of the autonomous sampling devices.

* * * * *